US00PP22758P2

(12) United States Plant Patent
Bradford

(10) Patent No.: US PP22,758 P2
(45) Date of Patent: May 29, 2012

(54) NECTARINE TREE NAMED 'PEARLICIOUS I'

(50) Latin Name: *Prunus persica*
Varietal Denomination: Pearlicious I

(76) Inventor: Lowell Glen Bradford, Le Grand, CA (US)

( * ) Notice: Subject to any disclaimer, the term of this patent is extended or adjusted under 35 U.S.C. 154(b) by 9 days.

(21) Appl. No.: 12/928,440

(22) Filed: Dec. 13, 2010

(51) Int. Cl.
*A01H 5/00* (2006.01)

(52) U.S. Cl. ..... Plt./188

(58) Field of Classification Search ..... Plt./188
See application file for complete search history.

(56) References Cited

U.S. PATENT DOCUMENTS

| | | | |
|---|---|---|---|
| PP7,507 | P | 4/1991 | Bradford |
| PP14,249 | P2 | 10/2003 | Bradford |
| PP17,254 | P2 | 12/2006 | Bradford |
| PP17,750 | P2 | 5/2007 | Bradford |

*Primary Examiner* — Susan McCormick Ewoldt

(57) ABSTRACT

The present invention relates to a new and distinct variety of nectarine tree, *Prunus persica*, broadly characterized by a medium size, moderately vigorous, half-hardy, self-fertile, very productive and regular bearing tree. The variety blooms early and requires about 350 chilling hours. The fruit matures under the ecological conditions described in early June, with first picking on Jun. 4, 2010. The fruit is uniformly large in size for an early season variety, globose in shape, clingstone in type, firm and melting in texture, white in flesh color, mostly red in skin color, and a tasty balance of sweet sub-acid and traditional nectarine flavors.

1 Drawing Sheet

Botanical classification: *Prunus persica.*
Variety denomination: 'Pearlicious I'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Pearlicious I'.

The present variety was hybridized by me in 2004 as a first generation cross using 'Candy Pearl' (U.S. Plant Pat. No. 14,249) nectarine as the selected seed parent and 'Spring princess' (U.S. Plant Pat. No. 17,750) peach as the selected pollen parent. The fruit of this cross was gathered in the spring of 2004, and the seeds were removed from the fruit, germinated, stratified, and grown as seedlings on their own root in my greenhouse. Upon reaching dormancy that winter, the seedlings were transplanted as a group to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Candy Pearl' nectarine by producing nectarines that are mostly red in skin color, white in flesh color, clingstone in type, mostly sub-acidic and sweet in flavor, firm in texture, and large in size, but is distinguished therefrom by requiring much less dormant chilling, by blooming earlier, and by producing fruit that is more symmetrical in shape and that matures about thirty days earlier.

The present variety is similar to its pollen parent, 'Spring Princess' peach by requiring a low amount of dormant chilling, by blooming in the early season, and by producing fruit that is clingstone in type and large in size, but is quite distinguished therefrom by being a white flesh nectarine instead of a yellow flesh peach.

The present variety is most similar to 'May Pearl' (U.S. Plant Pat. No. 17,254) nectarine by producing nectarines that are white in flesh color, clingstone in type, firm in texture, and mostly sub-acidic in flavor, but is distinguished therefrom by requiring slightly less chilling hours, by having reniform instead of globose leaf glands, and by producing fruit that is larger in size, that is a fuller red in skin color, and that matures about ten days later.

SUMMARY OF VARIETY

In summary, the present nectarine variety is characterized by a medium size, moderately vigorous, half-hardy, self-fertile, very productive and regular bearing tree. The variety blooms early and requires about 350 chilling hours. The fruit matures under the ecological conditions described in early June, with first picking on Jun. 4, 2010. The fruit is uniformly large in size for an early season variety, globose in shape, clingstone in type, firm and melting in texture, white in flesh color, mostly red in skin color, and a tasty balance of sweet sub-acid and traditional nectarine flavors.

DRAWING

The accompanying photograph consists of four whole fruits positioned to display the characteristics of the skin color and form, one divided fruit to reveal the flesh and stone, two insets to reveal buds and a blossoms, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 10, 2010, on the original tree during its sixth growing season. The blossom and flower descriptions were made the previous blooming season. All major color code designations are by reference to the Inter-Society Color Council, National Bureau of Standards. Common color names are also used occasionally.

It is to be noted that the climatic conditions in 2010 led to delayed blooming and delayed fruit ripening for most of the season by approximately ten days. This should be taken into account when comparing to other variety descriptions made referencing different years. However, the relative blooming times and ripening times cited in this application are accurate for 2010, and should remain about the same in future years.

Parentage

Seed parent: 'Candy Pearl' nectarine (U.S. Plant Pat. No. 14,249).

Pollen parent: 'Spring Princess' peach (U.S. Plant Pat. No. 17,750).

Tree

Size: Medium, reaching and maintaining a height of 12' [3.66 m.] and a spread of 7' [2.13 m.] after six growing seasons utilizing typical dormant pruning.

Vigor: Moderately vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Half-hardy with respect to central California winters.

Approximate chilling requirement: 375 hours.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Trunk:

- *Size*.—Medium, reaching a maximum diameter of 4⅝" [117.5 mm.] after the sixth growing season.
- *Texture*.—Shaggy.
- *Bark color*.—A Deep brown [56. deep Br] and Grayish brown [61. gy.Br] variegation with Moderate yellowish brown [77. m.yBr] crevices.
- *Lenticels*.—Approximate Number Per Square Inch: 10. Color: Dark orange yellow [72. d.OY]. Average Size: ⅜" [9.5 mm.]. Shape: Eye-shaped, elongated.

Branches:

- *Size*.—Diameter of limb is 2¾" [69.9 mm.] measured 12" above the crotch, 1½" [38.1 mm.] measured 12" above the first fork.
- *Texture*.—Smooth on first year wood, increasing roughness with age.
- *Color*.—Second Year Wood: Strong brown [55. s.Br].
- *Lenticels*.—Number Per Square Inch: About 60 on second year wood. Color: Light yellowish brown [76. l.yBr]. Average size: 1/16" [1.6 mm.] on second year wood. Shape: Eye-shaped, elongated.

Leaves:

- *Size*.—Medium. Average Length: 5" [127 mm.]. Average Width: 1 9/16" [39.7 mm.].
- *Arrangement*.—Alternate.
- *Thickness*.—Medium.
- *Form*.—Elliptical.
- *Apex*.—Acuminate.
- *Base*.—Rounded to obtuse.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Vein color*.—Light yellow green [119. l.YG].
- *Petiole*.—Average Length: 5/16" [7.9 mm.]. Average Thickness: 3/32" [2.4 mm.]. Color: Strong yellow green [117. s.YG].
- *Stipules*.—Number: Usually 2 per leaf, up to 6 per growing tip. Average Length: ¼" [6.4 mm.]. Color: Light yellow green [119. l.YG] becoming Deep reddish brown [41. deep rBr] with maturity.
- *Glands*.—Number: 1 to 4 per leaf. Position: Mostly alternate. Size: Medium. Form: Reniform. Color: Light yellow green [119. l.YG] becoming Grayish red [19. gy.R] with age.
- *Leaf buds*.—Pointed, medium in size.

Flower buds:

- *Hardiness*.—Half-hardy, with respect to central California winters.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Moderate purplish pink [250. m.pPk].

Flowers: Perfect, complete, perigynous, usually a single pistil, about thirty stamens, five sepal and petal locations alternately positioned.

- *Type*.—Showy, large.
- *Average flower diameter*.—1 15/16" [49.2 mm.].
- *Number of petals*.—Mostly five, extra petal fragments or double blossoms are rarely observed.
- *Petal shape*.—Circular to oval.
- *Petal margin*.—Entire, slightly wavy.
- *Average petal diameter*.—¾" [19.1 mm.].
- *Average petal length*.—¾" [19.1 mm.].
- *Petal apex*.—Rounded.
- *Petal base*.—Rounded to somewhat truncate.
- *Petal color*.—Pale purplish pink [252. p.pPk] toward the apex, Deep purplish pink [248. deep pPk] toward the base on both sides.

*Anther color*.—Strong red [12. s.R] over a Light yellow [86. l.Y] center at bloom onset.
*Stigma color*.—Pale yellow green [121. p.YG].
*Sepal color*.—Dark purplish red [259. d.pR] on the outer surface.
*Sepal length*.—¼" [6.4 mm.].
*Sepal width*.—3/16" [4.8 mm.].
*Sepal apex*.—Rounded to elliptical to match the sepal length and width.
*Sepal margin*.—Fairly smooth.
*Average pistil length*.—¾" [19.1 mm.].
*Average stamen length*.—9/16" [14.3 mm.].
*Fragrance*.—Moderate.
*Blooming period*.—Early, nine days before 'Spring Bright' (U.S. Plant Pat. No. 7,507) nectarine.
*Onset of bloom*.—One percent on Feb. 10, 2010.
*Date of full bloom*.—Feb. 17, 2010.
*Duration of bloom*.—One to two weeks, dependent on ambient temperature.
*Number per cluster*.—1 to 3 with single flowers most common.

Fruit

Maturity when described: Firm ripe, Jun. 10, 2010.
Date of first picking: Jun. 4, 2010.
Date of last picking: Jun. 14, 2010.
Size: Uniform, large.
*Average diameter axially*.—2⅝" [66.7 mm.].
*Average diameter across cheek plane*.—2⅞" [73 mm.].
*Average diameter across suture plane*.—2 13/16" [71.4 mm.].
*Typical weight*.—6.7 ounces [190 grams].
Form: Uniform, globose compressed axially.
*Longitudinal section form*.—Oblate.
*Transverse section through diameter*.—Round.
Suture: Extends from the base, continues along the side, and ends just past the pistil point.
*Near the base*.—A shallow groove.
*Along the side*.—A shallow trough.
*Near the apex*.—A shallow groove.
Ventral surface: Rounded, lipped stronger toward the apex.
Lips: Slightly unequal.
Cavity: Flaring, elongated in the suture plane, suture showing on one side, Very greenish yellow [97. v.gY] stem markings typical.
*Depth*.—½" [12.7 mm.].
*Breadth*.—15/16" [23.8 mm.].
Base: Rounded to slightly truncate, slightly cordate if viewed parallel to the suture.
Apex: Rounded to slightly truncate, cordate if viewed parallel to the suture.
Pistil point: An inconspicuous Deep reddish orange [36. deep rO] dot, negligible in length, depressed within the suture.
Stem: Medium.
*Average length*.—7/16" [11.1 mm.].
*Average width*.—3/16" [4.8 mm.].
Skin:
*Thickness*.—Medium.
*Surface*.—Smooth.
*Tenacity*.—Tenacious to flesh.
*Astringency*.—Nonastringent.
*Tendency to crack*.—None observed in a dry season.
*Color*.—Dark red [16. d.R] over a Dark reddish orange [38. d.rO] background with Light Moderate orange yellow [71. m.OY] freckling mostly toward the apex.
Flesh:
*Color*.—White [263. White] toward the skin, Greenish white [153. gWhite] very close to the stone.
*Surface of pit cavity*.—Covered with Yellowish white [92. yWhite] broken fibers when twisted from the stone.
*Amygdalin*.—Slight.
*Juice*.—Moderate, rich.
*Texture*.—Firm, tough, meaty.
*Fibers*.—Abundant, fine, tender.
*Ripens*.—Fairly evenly, slightly earlier at the apex.
*Flavor*.—Sub-acidic and sweet, typically 14 to 20 brix, balanced with a slight traditional nectarine flavor.
*Aroma*.—Slight.
*Eating quality*.—Very good.

Stone

Type: Clingstone.
Form: Obovate.
Hilum: Narrow, oval.
Base: Straight, slightly rounded.
Apex: Acuminate.
Sides: Somewhat unequal.
Surface: Irregularly furrowed toward the apex, pitted toward the base.
Ridges: Rounded.
External color: Moderate orange yellow [71. m.OY].
Pit wall color when cracked: Pale orange yellow [73. p.OY].
Cavity surface color: Light orange yellow [70. l.OY].
Average pit wall thickness: 3/16" [4.8 mm.].
Average width: 1 1/16"" [27 mm.].
Average length: 1 7/16" [36.5 mm.].
Average breadth: ¾" [19.1 mm.].
Tendency to split: None observed.
Kernel:
*Form*.—Oval.
*Skin color*.—Deep orange yellow [69. deep OY] when first removed.
*Pellicle color*.—Strong yellowish brown [74. s.yBr].
*Vein color*.—Strong brown [55. s.Br].
*Taste*.—Fairly sweet.
*Viable*.—Yes.
*Average width*.—7/16" [11.1 mm.].
*Average length*.—⅝" [15.9 mm.].
*Amygdalin*.—Scant.

Use

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'May Pearl' (U.S. Plant Pat. No. 17,254) nectarine by producing nectarines that are white in flesh color, clingstone in type, firm in texture, and mostly sub-acidic in flavor, but is distinguished therefrom by requiring slightly less chilling hours, by having reniform instead of globose leaf glands, and by producing fruit that is larger in size, that is a fuller red in skin color, and that matures about ten days later.

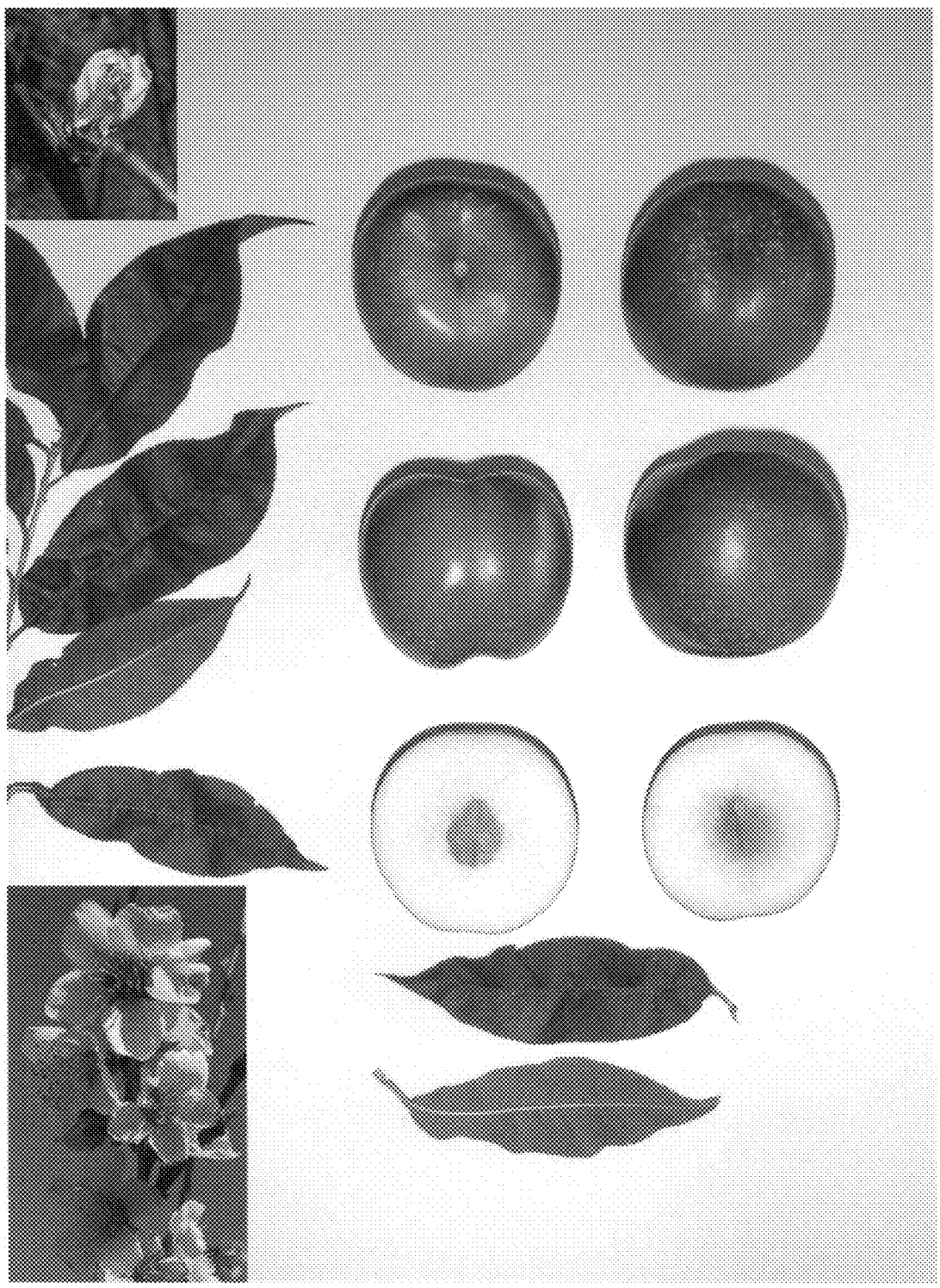

* * * * *